United States Patent [19]

Lapsley et al.

[11] Patent Number: 5,737,439

[45] Date of Patent: Apr. 7, 1998

[54] ANTI-FRAUD BIOMETRIC SCANNER THAT ACCURATELY DETECTS BLOOD FLOW

[75] Inventors: Philip Dean Lapsley, Oakland; Jonathan Alexander Lee, Berkeley; David Ferrin Pare, Jr., Berkeley; Ned Hoffman, Berkeley, all of Calif.

[73] Assignee: SmartTouch, LLC., Berkeley, Calif.

[21] Appl. No.: 739,313

[22] Filed: Oct. 29, 1996

[51] Int. Cl.$^6$ .................................................. G06K 9/00

[52] U.S. Cl. ................................... 382/115; 382/128

[58] Field of Search ................................ 382/115, 116, 382/124, 128; 356/71; 340/825.31, 825.34; 128/666, 687; 902/3

[56] References Cited

U.S. PATENT DOCUMENTS

| | | | |
|---|---|---|---|
| 3,639,905 | 2/1972 | Yaida et al. | 340/825.34 |
| 4,537,484 | 8/1985 | Fowler et al. | 354/62 |
| 4,544,267 | 10/1985 | Schiller | 356/71 |
| 4,699,149 | 10/1987 | Rice | 128/664 |
| 4,720,869 | 1/1988 | Wadia | 382/2 |
| 4,728,186 | 3/1988 | Eguchi et al. | 356/71 |
| 4,784,484 | 11/1988 | Jensen | 356/71 |
| 5,073,950 | 12/1991 | Colbert | 382/2 |
| 5,077,803 | 12/1991 | Kato et al. | 382/4 |
| 5,088,817 | 2/1992 | Igaki et al. | 356/71 |
| 5,103,486 | 4/1992 | Grippi | 382/4 |
| 5,230,025 | 7/1993 | Fishbine et al. | 382/4 |
| 5,335,288 | 8/1994 | Faulkner | 382/4 |
| 5,386,104 | 1/1995 | Sime | 235/379 |

Primary Examiner—Andrew Johns
Attorney, Agent, or Firm—Ali Kamarei

[57] ABSTRACT

The invention discloses an anti-fraud biometric scanner that determines whether an object exhibits characteristics of blood flow consistent with that of a live human. The anti-fraud biometric scanner has biometric scanning means for obtaining a biometric sample from the object, blood flow detection means for determining whether the object exhibits characteristics of blood flow consistent with that of a live human, and deception detection means for determining if the object is attempting to deceive the blood flow detection means. The blood flow detection means comprises a first light source for illuminating the object, a photodetector for measuring light energy from the object, and computing means for controlling the first light source and processing output from the photodetector. The deception detection means provides means for detecting movement by the object in an attempt to deceptively simulate blood flow. The means for detecting movement uses the computing means and turns off the first light source, turns on a second light source, measures any time-varying light energy from the object, and, if the measured time-varying light energy is above a threshold, determines that fraud is occurring.

45 Claims, 4 Drawing Sheets

ANTI-FRAUD BIOMETRIC SCANNER THAT ACCURATELY DETECTS BLOOD FLOW

BACKGROUND OF THE INVENTION

The invention generally relates to biometric scanners, and more particularly to biometric scanners that can determine if an object being scanned exhibits characteristics of blood flow consistent with that of a live human.

Biometric scanners are used to provide security and authentication for computers, communications, and financial transactions. The biometrics used in these applications include fingerprints, hand geometry, retinal scans, and voice prints. Examples of patents in the field of fingerprint scanning include U.S. Pat. No. 5,230,025 to Fishbine et. al., U.S. Pat. No. 4,544,267 to Schiller, and U.S. Pat. No. 4,537,484 to Fowler et. al. Examples of patents in the field of hand geometry include U.S. Pat. No. 5,335,288 to Faulkner, U.S. Pat. No. 5,073,950 to Colbert et. al., and U.S. Pat. No. 4,720,869 to Wadia.

As biometric technology becomes more widely used to authenticate financial and other transactions, the opportunity for fraud by replicating an individual's biometric increases greatly. Unfortunately, existing biometric scanners can be easily deceived by the use of imposter body parts or other fraudulent mechanisms. For example, some fingerprint scanners can be deceived by a casting of a finger or fingerprint made from silicone or other pliable materials. Other fingerprint scanners can be fooled simply by placing a picture of a fingerprint over the scanner. Similarly, hand-geometry scanners can be fooled by a casting of a human hand. The problems posed by this fraud are large, and are especially severe when biometric scanners are used at unattended locations.

There have been attempts by others to detect the use of imposter fingers in fingerprint scanners. However, security problems have often been a key failing of these devices, as many such disclosed devices are relatively simple to deceive. For example, several disclosed devices attempt to detect blood flow in an object being scanned to determine if it is an imposter finger. An imposter finger can fool the disclosed devices using this approach by deceptively simulating blood flow. This simulation can be accomplished either through the use of a flashing light mounted on the imposter finger, or by motion on the part of the imposter finger. This is possible because previously disclosed devices detect variation in levels of reflected light energy from the object being scanned as evidence of blood flow. Thus, an object that emits light or that moves can confuse the disclosed devices into thinking that the object has blood flow. This problem has not been addressed in previous attempts to create fraud-resistant biometric scanners. User inconvenience is another issue that is often neglected. The techniques used in some devices either appreciably increase the time required to complete a biometric scan, or require an individual to perform extra steps to prove his or her authenticity. Still other approaches require actions that individuals find objectionable, such as squeezing the individual's finger to ascertain its veracity.

Finally, many of the disclosed devices are prohibitively expensive. For example, some require the use of costly optical components, such as lasers, polarizers, collimators, etc. Anti-fraud biometric scanners using such components are financially unattractive and thus impractical.

Therefore, it is an object of the invention to provide high security for biometric scanners by detecting whether an object being scanned exhibits characteristics of blood flow consistent with a live human.

Another objective of the invention is to provide high security in a way such that the scanner cannot be deceived by objects that emit light or move in an attempt to deceptively simulate blood flow.

Another objective of the invention is to provide a biometric scanners that does not require an individual to perform inconvenient or additional steps that appreciably increase the time required for completion of the scanning process.

Other objectives of the invention are to provide a high security biometric scanner using a minimum number of mechanical or electrical parts, and at a low cost.

SUMMARY

The invention discloses an anti-fraud biometric scanner that determines whether an object exhibits characteristics of blood flow consistent with that of a live human. The anti-fraud biometric scanner has biometric scanning means for obtaining a biometric sample from the object, blood flow detection means for determining whether the object exhibits characteristics of blood flow consistent with that of a live human, and deception detection means for determining if the object is attempting to deceive the blood flow detection means. The blood flow detection means comprises a first light source for illuminating the object, a photodetector for measuring light energy from the object, and computing means for controlling the first light source and processing output from the photodetector. The deception detection means provides means for detecting movement by the object in an attempt to deceptively simulate blood flow. The means for detecting movement uses the computing means to turn off the first light source, turn on a second light source, measure any time-varying light energy from the object, and, if the measured time-varying light energy is above a threshold, determine that fraud is occurring.

In another embodiment, the deception detection means comprises means for detecting whether the object emits light in an attempt to deceptively simulate blood flow. When the first light source is off, the computing means processes any measured light energy from the photodetector, and, if the measured light energy is above a threshold, determines that fraud is occurring.

The invention also discloses a method for rapidly determining whether an object presented to a biometric scanner exhibits characteristics of blood flow consistent with that of a live human, comprising the steps of illuminating the object with a first light source, measuring the light energy from the object to produce a first measurement, a blood flow detection step wherein the first measurement is processed to determine if the measurement is consistent with blood flow of a live human, and a deception detection step wherein attempts to deceive the blood flow detection step are detected.

The deception detection step extinguishes the first light source, measures the light energy emitted by the object while the first light source is extinguished to produce a second measurement, and determines that fraud is being attempted if the second measurement is above a threshold.

In another embodiment, the deception detection step extinguishes the first light source, illuminates the object with a second light source, and measures any time-varying light energy from the object while the first light source is extinguished to produce a third measurement, and determines that fraud is being attempted if the third measurement is above a threshold.

Accordingly, the invention is advantageous in that it provides high security for biometric scanners by detecting the use of an inanimate object posing as a live human body part such as a finger. The invention rapidly detects the presence or absence of blood flow consistent with a human body in the object being scanned.

Another advantage is that the invention provides this security in a way that cannot be deceived by an object emitting light or moving in an attempt to deceptively simulate blood flow.

A further advantage is that this security is provided with minimum inconvenience to the user. No additional steps are required on the part of the user to prove his or her authenticity, nor is the time required to complete a biometric scan appreciably increased.

An additional advantage is that the invention provides this security at low cost by using inexpensive components.

Still another advantage is that the invention provides this security with a minimum number of mechanical or electrical parts. Several embodiments leverage components that are already present in existing biometric scanners.

Further objects and advantages will become apparent from a consideration of the drawings and ensuing description.

DETAILED DESCRIPTION

The invention comprises biometric scanning means for obtaining a biometric sample from an object being scanned, blood flow detection means for detecting if the object being scanned exhibits characteristics of blood flow consistent with that of a live human, and deception detection means for determining if the object being scanned is attempting to deceive the blood flow detection means.

Figure 1:
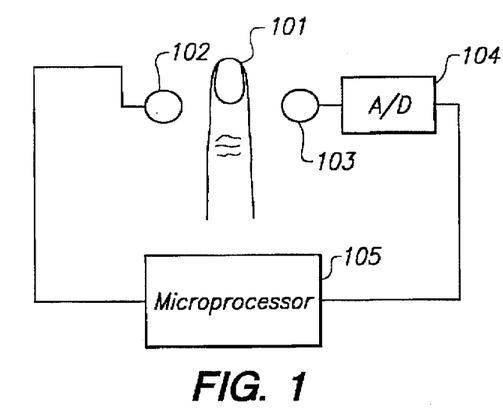
FIG. 1 shows a block diagram of an embodiment of the invention.

As shown in FIG. 1, a finger or other object 101 to be scanned is illuminated by a red light-emitting diode (LED) 102 that is connected to a computing means or microprocessor 105. A photodetector 103 converts light transmitted through or reflected from the object being scanned to an electrical signal. The photodetector is electrically connected to an A/D converter 104, which is in turn electrically connected to the microprocessor. These components are in turn attached to or integrated with a conventional biometric scanner (not shown in the figure). The LED, photodetector, A/D converter, and microprocessor are used as both the blood flow detection means and the deception detection means in this embodiment.

Figure 2:
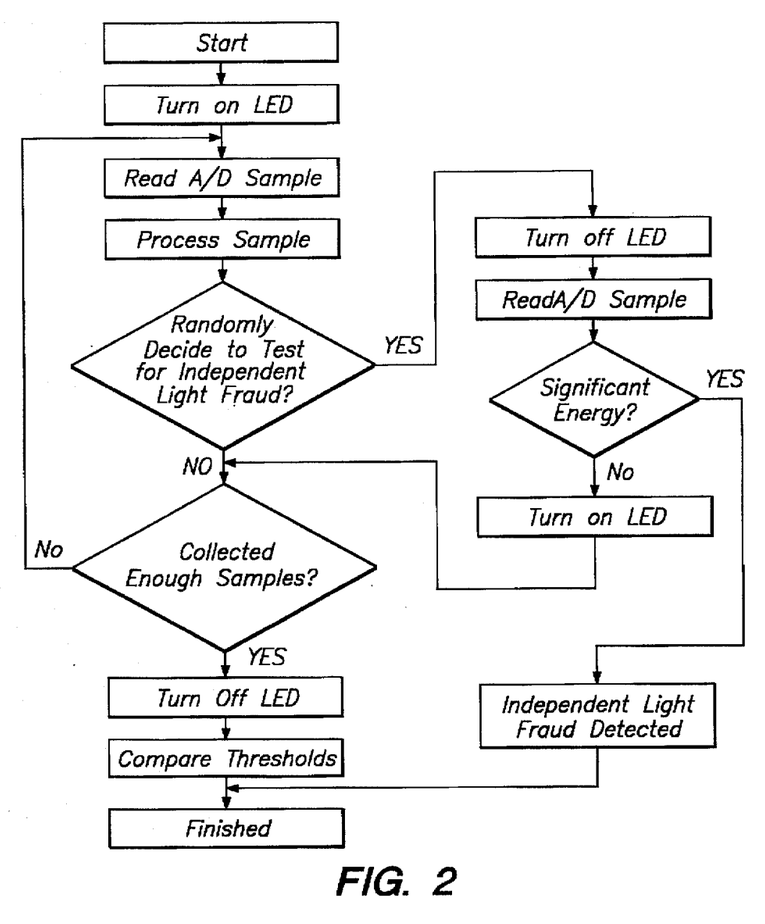
FIG. 2 shows a flow chart of the operation of an embodiment of the invention.

As illustrated by the flowchart in FIG. 2, the microprocessor turns on the LED to illuminate the object being scanned, such as a finger. In transmission mode, light is transmitted through the object; in reflectance mode, light reflects off of the object. In either case, the transmitted or reflected light impinges upon the photodetector.

The photodetector converts the incident light energy to an electrical signal, which is in turn sampled by the A/D converter under control of the microprocessor. The digital sample produced by the A/D converter is then processed by signal processing executed by the microprocessor to rapidly determine whether or not the object exhibits characteristics of blood flow consistent with that of a live human.

In one embodiment, the deception detection means comprises means for detecting whether the object emits light. This is done by comparing any measured light energy to a threshold. An object that emits light is inconsistent with a human body part. Thus, if it is determined that light energy levels above a threshold exist, then there is an attempt to deceive the blood flow detection means. In a preferred embodiment, the microprocessor generates a random number. If the random number is above a threshold, the microprocessor turns off the LED and measures the received light energy at the photodetector by reading another sample from the A/D converter. If the energy represented by this sample is above a threshold, indicating the presence of light from the object being scanned, then the microprocessor concludes that the object being scanned has a light source. Thus, there is an attempt to deceive the blood flow detection means. If no light source is detected, the microprocessor turns on the LED and continues processing as shown in FIG. 2.

In a preferred embodiment, the check for whether the object emits light is performed at least once per biometric scan, although the time during the scan at which it is performed is chosen at random.

The microprocessor next determines if it has accumulated a sufficient number of samples from the A/D converter to detect whether the object being scanned exhibits characteristics of blood flow consistent with that of a live human. In one embodiment, this decision is made based on the absolute number of samples acquired. In another embodiment, it is based both on the number of samples acquired and on their quality. For example, if the samples acquired from the A/D converter are particularly noisy, more samples may be required. If more samples are needed, the process repeats as indicated in FIG. 2. If no more samples need to be collected, the microprocessor turns off the LED and examines any outputs of the signal processing to determine whether or not the object being scanned exhibits characteristics of blood flow consistent with that of a live human.

Figure 3:
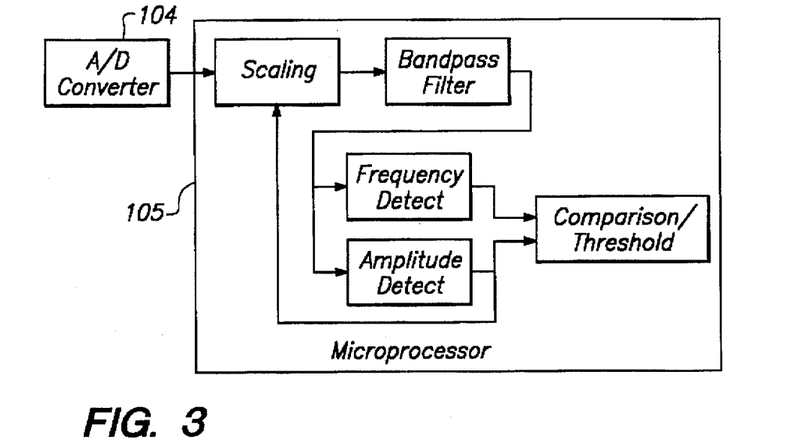
FIG. 3 shows a block diagram of signal processing used in an embodiment of the invention.

FIG. 3 shows a block diagram of the signal processing used in the blood flow detection means to extract characteristics such as the frequency and amplitude of the signal sampled by the A/D converter when the LED is on. The samples from the A/D converter are first scaled (increased or decreased in amplitude) by an amount set by automatic gain control processing. The samples are next bandpass-filtered to remove noise below approximately 0.3 Hz and above 3.3 Hz; these frequencies correspond to 20 and 200 heartbeats per minute. An alternate embodiment filters noise below a frequency corresponding to 40 heartbeats per minute, and above a frequency corresponding to 180 heartbeats per minute. The resulting signal is then processed to determine its frequency and amplitude. Frequency detection processing such as a phase-locked loop is used to detect the fundamental frequency of the signal, a mechanism well-known in the signal-processing art. An amplitude detector squares the signal samples and then low-pass filters the squared signal using an infinite-impulse-response (IIR) digital filter, producing an amplitude indication. The amplitude indication is then fed back to the automatic gain control processing to indicate the degree to which the input signal should be scaled up or down. The result of the frequency and amplitude detection are then made available for a determination by the microprocessor as to whether or not the frequency and amplitude values of the signal fall within minimum and maximum levels that are consistent with blood flow in a live human. Thus, by measuring the variation in transmitted or reflected red light, the invention rapidly determines if the object being scanned exhibits characteristics of blood flow consistent with that of a live human. In a preferred embodiment, this determination is made in less than about two seconds, and most preferably in less than about one second.

In another embodiment, any combination of a digital signal processor (DSP), a microcontroller, digital circuitry, or analog circuitry may be used instead of a microprocessor to control the elements of the invention and to implement signal processing. In yet another embodiment, the LED mentioned above could also be a laser diode or a simple incandesent lamp with a red-colored filter.

Other embodiments of the invention measure frequency via a finite impulse response (FIR) filter that is configured to act as a slope detector, or via a Kalman filter or an LMS adaptive FIR filter. In another embodiment, the amplitude detector uses the absolute value of the samples instead of their squares. These techniques are well known in the signal-processing art.

Figure 4:
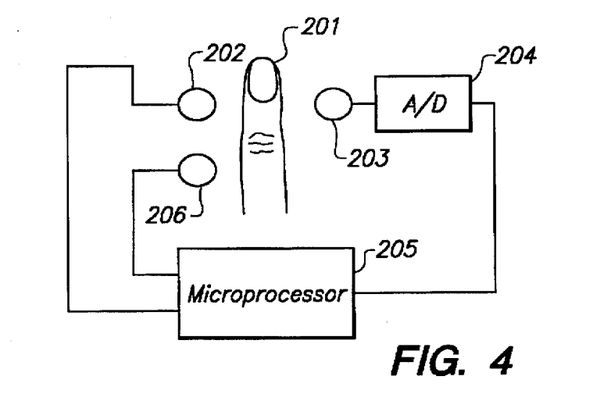
FIG. 4 shows a block diagram of an alternate embodiment of the invention.

FIG. 4 shows an alternate embodiment of the invention in which the deception detection means comprises means for detecting motion on the part of the object being scanned.

FIG. 4 shows two LEDs that are electrically connected to the microprocessor. The first LED 202 has a wavelength in the red portion of the spectrum, approximately 660 nm. The second LED 206 has a wavelength in the infrared portion of the spectrum, approximately 805 nm. The LEDs are used to illuminate a finger or other object 201 to be scanned. A photodetector 203 sensitive to light at the wavelengths produced by the first and second LEDs converts light reflected from or transmitted through the object being scanned to an electrical signal. The photodetector is electrically connected to an A/D 204, which is in turn electrically connected to the microprocessor 205. These components are in turn attached to or integral with a conventional biometric scanner (not shown in the figure). In this embodiment, the deception detection means uses the second LED to detect motion on the part of the object that might deceptively simulate blood flow.

The microprocessor turns on the first LED to illuminate the object being scanned. In transmission mode, light is transmitted through the object being scanned; in reflectance mode, light is reflected off of the object being scanned. In either case, the reflected or transmitted light then impinges upon the photodetector. The photodetector converts the incident light energy to an electrical signal, which is in turn sampled by the A/D converter under control of the microprocessor. The microprocessor then turns off the first LED and turns on the second LED, whereupon the sampling process outlined above is repeated. The digital samples produced by the A/D converter thus represent interleaved samples of the reflected or transmitted light in the red or infrared portions of the spectrum. These samples are then processed by signal processing executed by the microprocessor to rapidly determine whether or not the object being scanned has blood flow consistent with that of a live human. In particular, the invention rapidly produces indicia based on time-varying measurements such as the the amplitude and frequency of the signal corresponding to the time-varying energy of the reflected or transmitted red light, and determines whether or not significant energies at non-zero frequencies are present in the infrared light.

In a preferred embodiment, the microprocessor randomly turns off both LEDs and measures any received light energy at the photodetector. If the received light energy is above a threshold when the LEDs are off, the microprocessor concludes that the object is emitting light, which is inconsistent with that of a human body part. Thus, there is an attempt to deceive the blood flow detection means.

Figure 5:
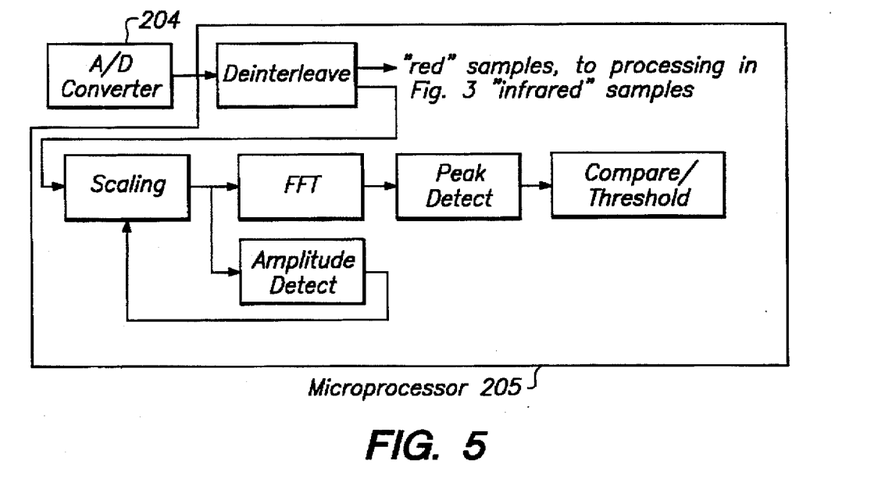
FIG. 5 shows a block diagram of signal processing used in another embodiment of the invention.

FIG. 5 shows a block diagram of the signal processing used in both the blood flow detection means and the deception detection means to extract characteristics such as frequency and amplitude of the signals produced by the A/D converter. As shown, samples from the A/D converter are first deinterleaved to produce a first stream of samples corresponding to transmitted or reflected red light energy, and a second stream of samples corresponding to transmitted or reflected infrared light energy. The "red light samples" are then processed as in FIG. 3 as described in the previous embodiment. The "infrared light samples" are then processed to measure their time-varying light energy. The samples are first scaled by an amount controlled by automatic gain control. The scaled samples are then fed into a fast Fourier transform (FFT) which measures the energy present at different frequencies. The FFT output is then examined for the presence of significant energies at frequencies other than DC (i.e., 0 Hz). The frequencies and amplitudes of the significant-energy, along with a count of the total number of significant-energy frequencies, are then used to compute an overall value indicating the periodicity and amplitude of the infrared energy. In one embodiment, this computation is performed by summing together the products of each non-zero-amplitude frequency and its amplitude. This output, along with the output of the red light processing, is fed into a comparison/threshold algorithm that determines whether or not the object being scanned exhibits characteristics of blood flow consistent with that of a live human.

An alternative embodiment uses a single bi-color LED to replace the two LEDs described above. The bi-color LED emits red light when electrically biased in one direction, and infrared light when electrically biased in the opposite direction. For example, in one embodiment a forward bias on the bi-color LED causes it to emit red light, and a reverse bias causes it to emit infrared light.

The descriptions of the embodiments that follow use two LEDs. However, it should be noted that either one or two single-color LEDs can be used in any of the embodiments described below.

Figure 6:
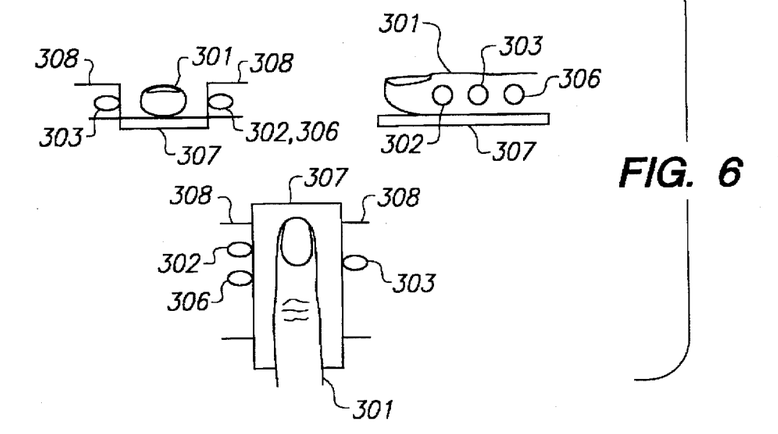
FIG. 6 shows an alternate embodiment of the invention comprising a fingerprint scanner that uses optical, capacitive, or acoustic imaging.

FIG. 6 shows an embodiment in which the biometric scanning means comprises a fingerprint scanner. The imaging surface 307 of the fingerprint scanner is attached to an enclosure 308 that secures the first LED 302 and second LED 306 and the photodetector 303. The photodetector is electrically connected to an A/D converter (not shown), and the A/D converter and LEDs are connected to a microprocessor (also not shown) as in FIG. 1. This embodiment shows transmission mode, but reflectance mode can be used as well. In one embodiment, the fingerprint scanner comprises a two-dimensional capacitance detector, forming a fingerprint image using capacitance. In another embodiment, the fingerprint scanner comprises an ultrasound transmitter for irradiating the object with ultrasonic energy, an ultrasound receiver for measuring ultrasonic energy reflected from the object, and ultrasound imaging means for converting electrical signals from the ultrasound receiver to another electrical signal that represents a two-dimensional image of the object.

In operation, a finger or other object 301 to be scanned is placed onto the imaging surface of the fingerprint scanner and between the enclosure and LEDs and photodetector. Preferably, as the fingerprint scanner scans the object, the microprocessor simultaneously determines whether or not the object exhibits characteristics of blood flow consistent with that of a live human in accordance with the methods of the invention.

In one embodiment, the microprocessor is a separate component from any microprocessor used in the fingerprint scanner, while in another embodiment the microprocessor is shared between the fingerprint scanner and the blood flow detection means.

Figure 7:
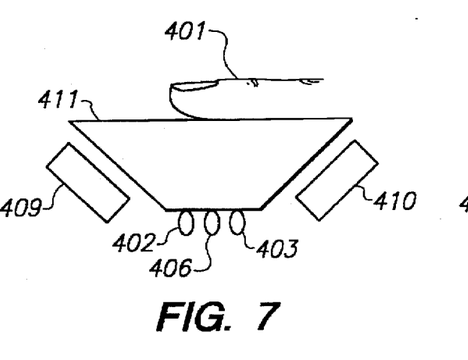
FIG. 7 shows an alternate embodiment of the invention comprising a conventional prism-based fingerprint scanner.

FIG. 7 shows an embodiment in which the biometric scanning means comprises a fingerprint scanner using a truncated prism 411. Light from the fingerprint imager light source 409 is modulated by the prism and an object 401 such as a finger and impinges upon the fingerprint imager CCD 410. The CCD forms an electronic signal representing an image of the object being scanned. The first LED 402 and second LED 406 illuminate the finger and the reflected light is measured by the photodetector 403.

In operation, an object to be scanned such as a finger 401, is placed onto the surface of the prism. The fingerprint imager light source illuminates the object and the fingerprint imager CCD forms an image of the object being scanned. The fingerprint imager light source is then turned off, and the microprocessor (not shown) uses the first and second LEDs and photodetector to determine whether or not the object being scanned exhibits characteristics of blood flow consistent with that of a live human in accordance with the methods of the invention. In an alternate embodiment, a CMOS image array replaces the CCD.

Figure 8:
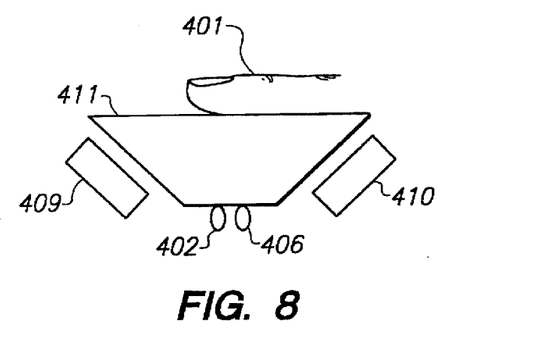
FIG. 8 shows an alternate embodiment of the invention comprising a conventional prism-based fingerprint scanner but that replaces the photodetector with a CCD.

FIG. 8 shows an alternate embodiment in which the photodetector and A/D converter (not shown) used in the blood flow detection means and the deception detection means are replaced by image conversion means which converts a two-dimensional image into an electrical signal, such as a CCD or CMOS image array.

The fingerprint imager CCD 410 is sensitive to the wavelengths of light produced by both the first and second LEDs. In this embodiment a microprocessor is connected to the fingerprint imager CCD. The microprocessor sums or averages the values of all the individual pixels in the CCD. This yields a single number whose value is proportional to the energy of the light impinging on the surface of the CCD. Thus, the CCD functions as "one large photodetector."

In operation, a finger or other object to be scanned is placed onto the surface of the prism. The fingerprint imager illuminates the object via the fingerprint imager light source, and the fingerprint imager CCD forms an image of the object. The fingerprint imager light source is then turned off, and the microprocessor (not shown) uses the first and second LEDs and the fingerprint imager CCD to determine whether or not the object being scanned exhibits characteristics of blood flow consistent with that of a live human in accordance with the methods of the invention.

Figure 9:
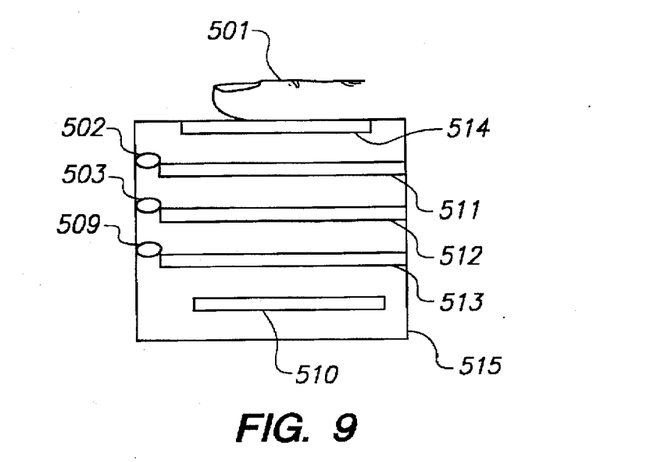
FIG. 9 shows an alternate embodiment of the invention comprising a fingerprint scanner that uses edge-lit holography.

FIG. 9 shows an embodiment of the invention in which the biometric scanning means comprises a fingerprint scanner that makes use of edge-lit holography (Metz, CardTech/SecureTech Conference Proceedings, 1995). An optically transparent window 514 is provided on which a finger or other object to be scanned 501 rests during scanning. Three illumination sources are used: a first LED 502, a second LED 503, and a fingerprint imager light source 509. Each illumination source is paired with an edge-lit hologram (511, 512, and 513, respectively) that redirects or bends light energy by roughly 90 degrees when it is illuminated from its side. A fingerprint imager CCD 510 converts light energy reflected from the finger to either an image of the fingerprint or an indication of the reflected energy from the first or second LED, as in the previous embodiment. The device is encased in an enclosure 515.

In operation, a finger or other object to be scanned is placed onto the window. The fingerprint imager then turns on the fingerprint imager LED. The third edge-lit hologram then redirects the light energy from the LED up towards the finger, where it passes through the first and second edge-lit holograms, reflects off the finger, again passes through the first and second edge-lit holograms, and impinges upon the fingerprint imager CCD, forming an image of the object.

The fingerprint imager then turns off the fingerprint imager LED, and uses the first and second LEDs in conjunction with the first and second edge-lit holograms and the fingerprint imager CCD to determine whether or not the object being scanned exhibits characteristics of blood flow consistent with that of a live human in accordance with the methods of the invention.

Another embodiment uses only two holograms and LEDs. In this embodiment, one of the first or second LEDs and edge-lit holograms are used both for illumination for the fingerprint imager and for detection of blood-flow characteristics.

Figure 10:
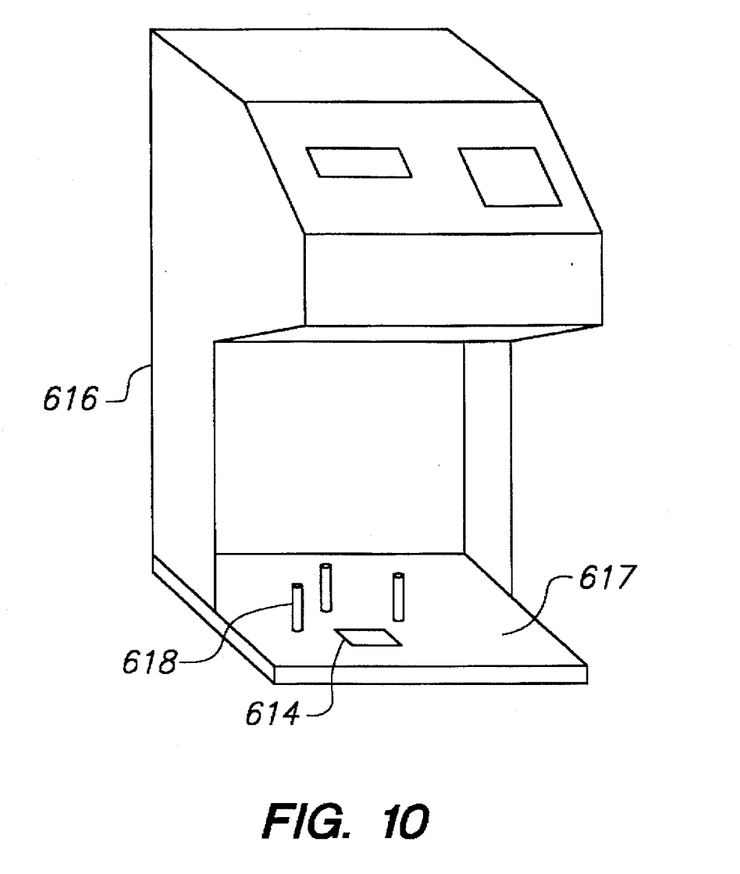
FIG. 10 shows an alternate embodiment of the invention comprising a hand geometry scanner.
Figure 11:
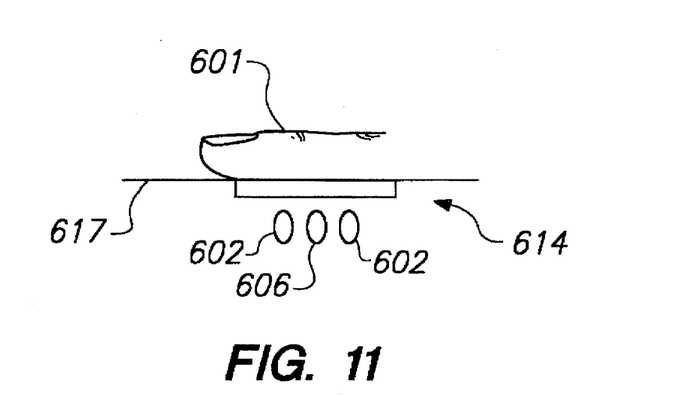
FIG. 11 shows a side view of the blood flow and sensors of the deception detection means of the embodiment shown in FIG. 10.

FIGS. 10 and 11 show an embodiment of the invention in which the biometric scanning means comprises a hand geometry scanner 616. A surface 617 is provided on which a hand or other object to be scanned 601 is placed. Guide posts 618 are also provided that are used to provide proper finger alignment. The surface on which the hand rests also includes an optically transparent window 614, beneath which are a first LED 602, a second LED 606, and a photodetector 603. These are arranged such that light from the LEDs is reflected off the bottom surface of the object being scanned (e.g., the palm of an individual's hand), where it is measured by the photodetector. As in previously described embodiments, a microprocessor (not shown) controls the LEDs and processes the output of the photodetector to rapidly determine if the object being scanned exhibits characteristics of blood flow consistent with that of a live human.

In another embodiment, multiple LEDs and photodetectors are used to observe the hand or other object being scanned from several angles and positions. It is advantageous to make observations from several locations, including the upper portion of the recessed area in the hand geometry detector. In such an embodiment, ambient light causes a reduction in the received signal-to-noise ratio present at the photodetector. This is overcome by the addition of a second photodetector whose purpose is to measure the ambient light energy alone. Adaptive signal processing techniques that are well-known in the signal processing art are then used to increase the signal-to-noise ratio at the first photodetector.

What is claimed is:

1. An anti-fraud biometric scanner that determines whether an object exhibits characteristics of blood flow consistent with that of a live human, comprising:
   a) biometric scanning means for obtaining a biometric sample from the object;
   b) blood flow detection means for determining whether the object exhibits characteristics of blood flow consistent with that of a live human; and
   c) deception detection means for determining if the object is attempting to deceive the blood flow detection means.

2. The apparatus of claim 1 wherein the blood flow detection means comprises:
   a) a first light source for illuminating the object;
   b) a photodetector for measuring light energy from the object; and
   c) computing means for controlling the first light source and processing output from the photodetector.

3. The apparatus of claim 2 wherein the deception detection means comprises means for detecting movement by the object in an attempt to deceptively simulate blood flow.

4. The apparatus of claim 3 wherein the means for detecting movement comprises a second light source, and wherein the computing means turns off the first light source, turns on the second light source, measures any time-varying light energy from the object, and, if the measured time-varying light energy is above a threshold, determines that fraud is being attempted.

5. The apparatus of claim 4 wherein the second light source has a wavelength of approximately 805 nm.

6. The apparatus of claim 4 wherein the second light source is a light-emitting diode.

7. The apparatus of claim 2 wherein the deception detection means comprises means for detecting whether the object emits light in an attempt to deceptively simulate blood flow.

8. The apparatus of claim 7 wherein when the first light source is off, the computing means processes any measured light energy from the photodetector, and, if the measured light energy is above a threshold, determines that fraud is being attempted.

9. The apparatus of claim 2 wherein the first light source has a wavelength of approximately 660 nm.

10. The apparatus of claim 2 wherein the first light source comprises a light-emitting diode.

11. The apparatus of claim 2 wherein the first light source comprises a bi-color light-emitting diode.

12. The apparatus of claim 11 wherein the bi-color light-emitting diode produces light at a wavelength of approximately 660 nm when electrically biased in a first direction, and light at a wavelength of approximately 805 nm when electrically biased in the opposite direction.

13. The apparatus of claim 2 wherein the computing means is selected from the group comprising: a microprocessor, a microcontroller, a digital signal processor, digital logic circuitry, analog circuitry.

14. The apparatus of claim 2 wherein the first light source and the photodetector are arranged such that light from the first light source is transmitted through the object and impinges upon the photodetector.

15. The apparatus of claim 2 wherein the first light source and the photodetector are arranged such that light from the first light source is reflected from the object and impinges upon the photodetector.

16. The apparatus of claim 2 wherein the photodetector comprises an image-conversion means for converting a two-dimensional image into an electrical signal.

17. The apparatus of claim 16 wherein the image-conversion means is a CCD.

18. The apparatus of claim 16 wherein the image-conversion means is a CMOS image array.

19. The apparatus of claim 2 wherein the first light source is a bi-color light-emitting diode.

20. The apparatus of claim 19 wherein the deception detection means comprises means for detecting movement by the object in an attempt to deceptively simulate blood flow.

21. The apparatus of claim 20 wherein the computing means electrically biases the bi-color light-emitting diode to produce infrared light, measures any time-varying light energy from the object, and, if the measured time-varying light energy is above a threshold, determines that fraud is being attempted.

22. The apparatus of claim 19 wherein the deception detection means comprises means for detecting whether the object emits light in an attempt to deceptively simulate blood flow.

23. The apparatus of claim 22 wherein when the first light source is off, the computing means processes any measured light energy from the photodetector, and, if the measured light energy is above a threshold, determines that fraud is being attempted.

24. The apparatus of claim 1 wherein the biometric scanning means comprises a fingerprint scanner.

25. The apparatus of claim 24 wherein the fingerprint scanner comprises:
   a) a prism on which the object rests,
   b) a fingerprint scanner light source for illuminating the object, and
   c) a fingerprint scanner image-conversion means for converting a two-dimensional image of the object to an electrical signal.

26. The apparatus of claim 24 wherein the fingerprint scanner comprises a two-dimensional capacitance detector, whereby a fingerprint image is formed using capacitance.

27. The apparatus of claim 24 wherein the fingerprint scanner comprises:
   a) a transparent surface on which the object is placed,
   b) at least two holograms for redirecting light incident at an angle substantially parallel to the surface of the holograms to an angle of about 90 degrees to the surface of the holograms,
   c) a fingerprint scanner light source for illuminating the holograms at an angle substantially parallel to the surface of the holograms, and
   d) an image-conversion means for converting a two-dimensional image of the object to an electrical signal.

28. The apparatus of claim 24 wherein the fingerprint scanner comprises:
   a) a surface on which the object is placed,
   b) an ultrasound transmitter for irradiating the object with ultrasonic energy,
   c) an ultrasound receiver for measuring ultrasonic energy reflected from the object, and d) an ultrasound imaging means for converting electrical signals from the ultrasound receiver to another electrical signal that represents a two-dimensional image of the object, whereby a fingerprint image is formed using ultrasonic energy.

29. The apparatus of claim 1 wherein the biometric scanning means comprises a hand geometry scanner.

30. An anti-fraud biometric scanner that determines whether an object exhibits characteristics of blood flow consistent with that of a live human, comprising:
 a) biometric scanning means for obtaining a biometric sample from the object;
 b) blood flow detection means for determining whether the object exhibits characteristics of blood flow consistent with that of a live human; and
 c) means for detecting movement by the object in an attempt to deceptively simulate blood flow.

31. An anti-fraud biometric scanner that determines whether an object exhibits characteristics of blood flow consistent with that of a live human, comprising:
 a) biometric scanning means for obtaining a biometric sample from the object;
 b) blood flow detection means for determining whether the object exhibits characteristics of blood flow consistent with that of a live human; and
 c) means for detecting whether the object has a light source that it is using in an attempt to deceptively simulate blood flow.

32. An anti-fraud biometric scanner that determines whether an object exhibits characteristics of blood flow consistent with that of a live human, comprising:
 a) biometric scanning means for obtaining a biometric sample from the object;
 b) blood flow detection means for determining whether the object exhibits characteristics of blood flow consistent with that of a live human, further comprising:
  i) a first light source for illuminating the object;
  ii) a photodetector for measuring light energy from the object;
  iii) computing means for controlling the first light source and processing output from the photodetector; and
 c) deception detection means wherein the computing means turns off the first light source, turns on an infrared light source, measures any time-varying light energy from the object, and determines that fraud is being attempted if the measured time-varying light energy is above a threshold.

33. An anti-fraud biometric scanner that determines whether an object exhibits characteristics of blood flow consistent with that of a live human, comprising:
 a) biometric scanning means for obtaining a biometric sample from the object,
 b) blood flow detection means for determining whether the object exhibits characteristics of blood flow consistent with that of a live human, further comprising:
  i) a light source for illuminating the object;
  ii) a photodetector for measuring light energy from the object;
  iii) computing means for controlling the light source and processing output from the photodetector; and
 c) deception detection means wherein the photodetector measures light energy emitted by the object when the light source is off, and wherein the computing means determines that fraud is being attempted if the measured light energy is above a threshold.

34. A method for rapidly determining whether an object presented to a biometric scanner exhibits characteristics of blood flow consistent with that of a live human, comprising the steps of:
 a) illuminating the object with a first light source,
 b) measuring the light energy from the object to produce a first measurement,
 c) a blood flow detection step, wherein the first measurement is processed to determine if the measurement is consistent with blood flow of a live human, and
 d) a deception detection step, wherein attempts to deceive the blood flow detection step are detected.

35. The method of claim 34 wherein the deception detection step comprises:
 a) extinguishing the first light source,
 b) measuring the light energy emitted by the object while the first light source is extinguished to produce a second measurement wherein it is determined that fraud is being attempted if the second measurement is above a threshold.

36. The method of claim 34 wherein the deception detection step comprises:
 a) extinguishing the first light source,
 b) illuminating the object with a second light source,
 c) measuring the time-varying light energy from the object while the first light source is extinguished and the object is illuminated with the second light source to produce a third measurement wherein it is determined that fraud is being attempted if the third measurement is above a threshold.

37. The method of claim 36 wherein the second light source has a wavelength of approximately 805 nm.

38. The method of claim 34 wherein the blood flow detection step further comprises the steps of:
 a) scaling the amplitude of the measured light energy, producing a scaled signal,
 b) filtering the scaled signal to remove low-frequency components, producing a filtered signal,
 c) measuring the frequency of the filtered signal, producing a frequency indication,
 d) measuring the amplitude of the filtered signal, producing an amplitude indication,
 e) comparing the frequency indication and the amplitude indication to thresholds to determine if they exhibit characteristics of blood flow consistent with that of a live human.

39. The method of claim 38 wherein the measurement of the frequency of the filtered signal is performed by a method selected from the following: a phase-locked loop, a Kalman filter, an LMS adaptive filter, or a slope-detecting filter.

40. The method of claim 38 wherein the measurement of the amplitude of the filtered signal comprises squaring the measured light energy.

41. The method of claim 38 wherein the measurement of the amplitude of the filtered signal comprises taking the absolute value of the measured light energy.

42. The method of claim 34 wherein the steps are repeated periodically.

43. The method of claim 34 wherein the deception detection step is executed at randomly selected times.

44. The method of claim 34 wherein the first light source has a wavelength of approximately 660 nm.

45. A method for rapidly determining whether an object presented to a biometric scanner exhibits characteristics of blood flow consistent with that of a live human, comprising the steps of:

a) illuminating the object with a first light source, b) measuring the light energy from the object to produce a first measurement, c) a blood flow detection step, wherein the first measurement is processed to determine if the first measurement is consistent with blood flow of a live human, and d) a deception detection step, wherein attempts to deceive the blood flow detection step are detected, further comprising:

i) extinguishing the first light source, ii) measuring the light energy emitted by the object while the first light source is extinguished to produce a second measurement, iii) illuminating the object with a second light source, iv) measuring the time-varying light energy from the object while the first light source is extinguished and the object is illuminated with the second light source to produce a third measurement wherein it is determined that fraud is being attempted if the second or third measurement is above a threshold.

* * * * *